United States Patent [19]

Stewart

[11] Patent Number: 4,561,426

[45] Date of Patent: Dec. 31, 1985

[54] MAGNETIC BIOLOGICAL DEVICE

[76] Inventor: David J. Stewart, R.R. #2, Loretto, Ontario, Canada, L0G 1L0

[21] Appl. No.: 654,945

[22] Filed: Sep. 27, 1984

[30] Foreign Application Priority Data

Feb. 29, 1984 [CA] Canada ................................. 448526

[51] Int. Cl.⁴ .............................................. A61B 17/52
[52] U.S. Cl. ................................: 128/1.5; 128/419 F
[58] Field of Search ................... 128/1.5, 420 R, 421, 128/419 F

[56] References Cited

U.S. PATENT DOCUMENTS

| | | | |
|---|---|---|---|
| 129,752 | 7/1872 | Sayer | 128/1.5 |
| 450,923 | 4/1891 | Woolley | 128/1.5 |
| 781,448 | 1/1905 | McIntyre | 128/1.5 |
| 3,055,372 | 9/1962 | Browner | 128/421 |
| 3,890,953 | 6/1975 | Kraus | 128/1.5 |
| 3,893,462 | 7/1975 | Manning | 128/1.5 |
| 3,924,641 | 12/1975 | Weiss | 128/421 |
| 4,066,065 | 1/1978 | Kraus | 128/1.5 |
| 4,177,796 | 12/1979 | Franco | 128/1.5 |
| 4,233,965 | 11/1980 | Fairbanks | 128/1.5 |
| 4,240,437 | 12/1980 | Church | 128/420 R |
| 4,266,533 | 5/1981 | Ryaby | 128/1.5 |
| 4,324,258 | 4/1982 | Greene | 128/421 |
| 4,338,945 | 7/1982 | Kosugi | 128/421 |

Primary Examiner—Peter D. Rosenberg
Attorney, Agent, or Firm—Riches, McKenzie & Herbert

[57] ABSTRACT

An electromagnetic device for modifying any of the growth, repair or maintenance processes in a predetermined local area of a living body by utilizing a signal having a symmetric waveform to excite a coil and thereby induce a magnetic field and at the same time manually or mechanically manipulating the coil so as to cause time variations in the spatial-orientation of the induced magnetic field with respect to the local area.

18 Claims, 3 Drawing Figures

MAGNETIC BIOLOGICAL DEVICE

BACKGROUND OF THE DISCLOSURE

This invention relates to electromagnetic devices and particularly to electromagnetic devices for modifying any of the growth, repair of maintenance processes in a predetermined local area of a living body.

Although the process is not fully understood, it is believed that if the electro-chemical equilibrium of a cell is somehow placed into a state of imbalance, the body will attempt to correct that imbalance. This correction by the body is believed to be the natural healing process of the body.

In the past, this cellular equilibrium has been artificially disrupted by means of magnetic fields applied to the subject cells. It is believed that if the magnetic field penetrates into the area of the subject cells and if the intensity of the magnetic field is varied, an induced electron movement and concomitant change in voltaic potential in or around the subject cells will result.

In prior art devices, the appropriate magnetic field was created by electrically exciting an electric coil with a signal having an asymmetrical waveform. A device that used a signal with a symmetrical waveform would not be as effective.

SUMMARY OF THE INVENTION

Accordingly, one broad aspect of this invention resides in providing an electromagnetic device for modifying any of the growth, repair or maintenance processes in a predetermined local area of a living body that utilizes a signal having a symmetric waveform to excite a magnetic-field-producing coil.

Another aspect of this invention resides in providing an electromagnetic device for modifying any of the growth, repair or maintenance processes in a predetermined local area of a living body comprising: a coil capable of inducing a magnetic field, wherein the magnetic field has a time-varying spatial-configuration and a time-constant spatial-orientation with respect to said coil; means for generating an electrical signal capable of exciting said coil so as to induce a magnetic field having a time-varying spatial-configuration, wherein said signal has a substantially-symmetric waveform; with a frequency below about 100 Hertz; and wherein, when said device is in use, said coil is adapted such that the spatial-orientation of said magnetic field with respect to said local area, is capable of being varied in time thereby causing time variations in said magnetic field at any given location in said local area which are of about the same range of magnitude as the time variations in the magnetic field at said any given location caused by the time variations in the spatial-configuration of said magnetic field.

Further aspects of the invention will become apparent from the following description of preferred embodiments of the invention.

BRIEF DESCRIPTION OF THE DRAWINGS

In the drawings which illustrate some embodiments and aspects of the invention.

DETAILED DESCRIPTION OF THE PREFERRED EMBODIMENTS OF THE INVENTION

Figure 1:
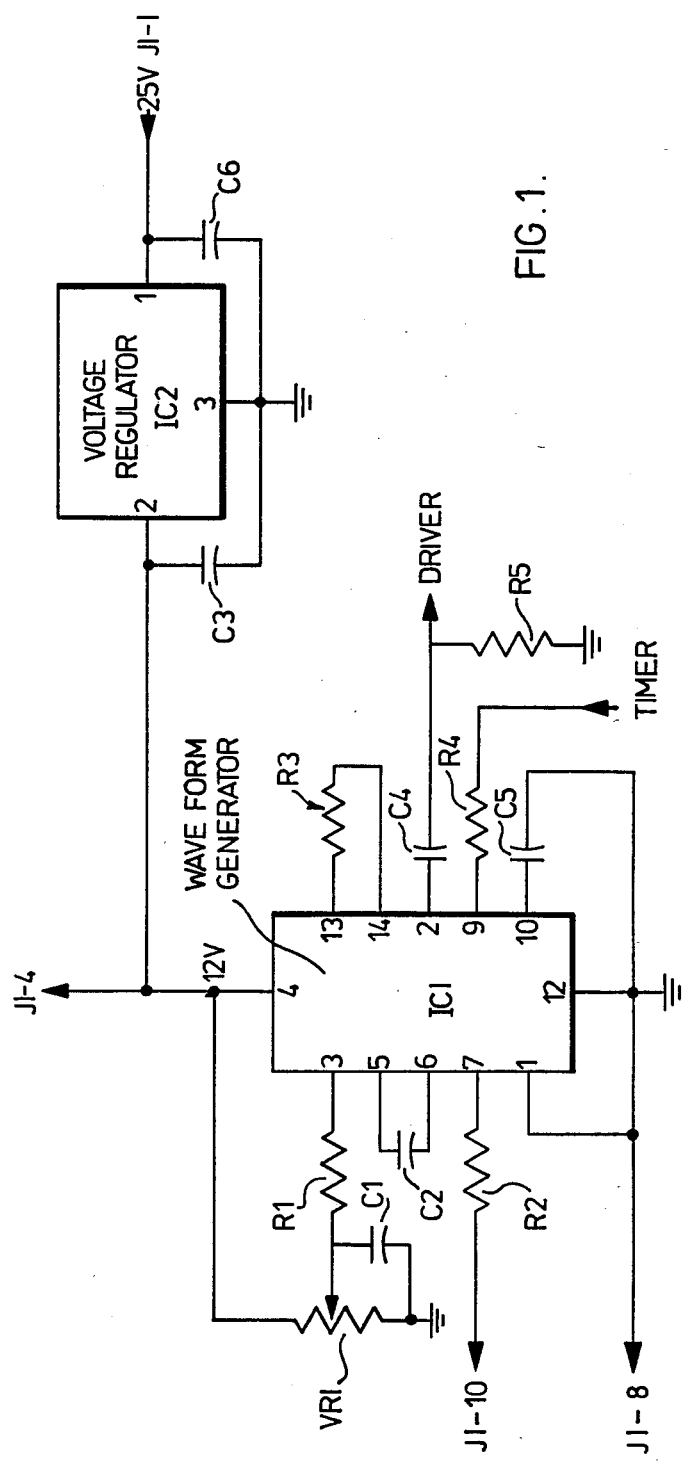
FIG. 1 is a schematic drawing of the circuit for an embodiment of the signal generator of the present invention.

With reference to the drawings, the concepts behind the invention as well as embodiments of the invention will be described. As noted above, it is believed that if the electro-chemical equilibrium of a cell is somehow disrupted or placed into a state of imbalance, the body will naturally attempt to correct that imbalance and that correction is believed to be the body's natural healing process. Thus, it is believed that if the electro-chemical equilibrium of cells can be temporarily imbalanced for sufficiently long periods, the body's natural healing processes can be artificially stimulated to correct the imbalance.

One way to artificially create an imbalance in the electro-chemical equilibrium of cells is to induce electron movement and a concomitant change in the voltaic potential in and around the cells. Such electron movement can be produced by applying to the cells a magnetic field having a time-varying spatial-configuration. As the magnetic intensity of the magnetic field rises and falls with time, an electron movement is believed to be induced which in turn causes a change in voltaic potential.

The spatial-configuration of a magnetic field is taken to mean or represent the spatial distribution, or all of the values, of the field throughout all points in space at any given instant in time. Thus, if a magnetic field has a time-constant spatial configuration, the value of the field at any given point in space remains the same or is constant throughout all time. However, all points in space do not necessarily have the same value at any given instant in time.

A time-varying spatial-configuration means that the value of the field at any given point in space varies or changes from one instant of time to the next.

In a magnetic field having a time-varying spatial-configuration which varies cyclically, the value of the field at any given point in space varies from one instant to the other but the sequence of values repeats during subsequent cyclic periods.

If a magnetic field is induced by a cyclically-changing current in an electric coil, the induced magnetic field will be cyclical in time. Moreover, if an exciting electric signal in a coil has a symmetric waveform, the spatial-configuration of the induced magnetic field will vary cyclically and symmetrically with time. Furthermore, because induced electron movement is proportional to the rate of change in the inducing magnetic field, if the spatial-configuration of an inducing magnetic field varies symmetrically with time, any induced electron movement in or around the subject cells will be equally positive and negative. Thus, any disruption of the electro-chemical equilibrium of the cells occurring during the positive portion of the cycle will be immediately cancelled or corrected during the negative portion. Therefore, no residual imbalance will result and the natural healing processes of the body will not be artificially stimulated.

On the other hand, if the exciting signal is asymmetrical, the magnitudes of the positive and negative movement of the electrons will be unequal even though there will be equal energy associated with the positive and negative portions of the cycle. Accordingly, it is postulated that if there is a threshold level of energy associated with cellular electrons which must be attained in order to cause some movement of the electrons there will be electron movement in one direction and correspondingly less movement in the other direction. Thus, there will be a residual imbalance respecting the electro-chemical equilibrium of the cells and there will be artificial stimulation of the body's natural healing process in order to correct this induced imbalance.

Previous research in this area has neglected to consider aspects of the electromagnetic phenomena associated with process-modifying devices other than the variation in time of the spatial-configuration of the magnetic field. The present invention takes advantage of another aspect of the electromagnetic phenomena. That other aspect is the variation in time of the spatial-orientation of the magnetic field.

By spatial-orientation is meant the orientation or location in space of the spatial-configuration of the magnetic field with respect to some point. Thus, a time-constant spatial-orientation of a magnetic field with respect to the coil means that the spatial-configuration of the magnetic field will always appear to be in the same position in space relative to the coil throughout at least the time period of interest.

Further, a time-constant spatial-orientation of a magnetic field with respect to a local area of a body means that the spatial-configuration of the magnetic field will always appear to be in the same position in space relative to the local area of the body throughout at least the time period of interest. Accordingly, a time-varying spatial-orientation of a magnetic field with respect to a local area of a body means that the position or orientation of the spatial-configuration of the magnetic field will vary or change in time with respect to the local area of the body even though the position of the spatial-configuration may remain time-constant with respect to the inducing coil.

The present invention utilizes the discovery that the electro-chemical equilibrium of the cells in a local area of a living body can be placed into a state of imbalance if the spatial-configuration of the magnetic field is symmetrically varied in time and at the same time the spatial-orientation of the magnetic field with respect to the local area is varied in time such that the time variations in the magnetic field at a given location in said local area caused by the time variations in the spatial-orientation of the magnetic field with respect to the local area are of about the same range of magnitude as the time variations in the magnetic field at the given location in said local area caused by time variations in the spatial-configuration of the magnetic field.

In a preferred embodiment of this invention, time variations in the spatial-orientation of the magnetic field with respect to a local area are caused by manually translating the inducing coil in the same plane over the area of interest. By translation is meant movement of the coil in a plane approximately parallel to the surface of the body over the local area of the body and having the coil aligned for maximum field penetration into the local area.

Alternatively or additionally, time variations in the spatial-orientation of the magnetic field with respect to the local area can be caused, in some instances, by rotation of the coil in a plane approximately parallel to the surface of the body over the local area of the body and having the coil aligned for maximum field penetration into the local area. Rotation is effective only when the spatial-configuration of the magnetic field is non-symmetrical in the plane of rotation, for instance, when the coil surrounds the middle finger of an "E"-shaped core as described below.

In a preferred embodiment of the invention, a treatment head is utilized. The treatment head comprises at least the coil. Usually, the treatment head will be a separate unit from the means for generating the exciting signal. However, with miniturization, it is possible that the means for generating the exciting signal would be included in the treatment head. In any case, the treatment head is electrically connected to the means for generating the exciting signal. Preferable this electrical connection is made by means of relatively-long, flexible electric wires or cables.

The treatment head can be made of molded plastic or any other suitable material. Also, the treatment head can be adapted, either during any molding process or later, to be conveniently gripped by a human hand. This adaption is intended to aid in easy manual manipulation of the treatment head.

Alternatively, the treatment head can be adapted to be mechanically manipulated by any suitable mechanical means.

Whether the coil or treatment head is translated or rotated either manually or mechanically, the movement of the coil or treatment head should be such as to cause time variations in said magnetic field at any given location in said local area which are of about the same range of magnitude as time variations in the magnetic field at said any given location caused by the time variations in the spatial-configuration of said magnetic field.

Improved results can be achieved by winding the coil around a magnetic core. Particularly improved results are obtained if the coil is wound around the middle finger of a magnetic core formed in the shape of an "E".

A preferred embodiment of this invention includes a means to generate a pulsed symmetric signal and, in particular, a half-wave-rectified sine wave.

It is believed that any symmetrical signal having a waveform with a non-zero differential with respect to time would be suitable. Similarly, any symmetrical signal having symmetric discontinuities would be suitable.

It is to be noted that the suitable signal need not be generated exclusively by the signal generating means per se. It is possible that a signal generated by the signal generating means could be suitably modified by the inherent electrical characteristics of the remainder of the device to produce a suitable signal.

Shown in FIG. 1 is a schematic diagram illustrating a wave-generating circuit capable of producing a half-wave-rectified sine wave. Shown below in Table I are typical parts used in the configuration of the circuit illustrated in FIG. 1.

TABLE I

| | |
|---|---|
| C1 | Capacitor, Electrolytic, 10 μfd. 16 V |
| C2 | Capacitor, Met. Film, 1.0 μfd. 63 V |
| C3 | Capacitor, Met. Film, .1 μfd. 100 V |
| C4 | Capacitor, Electrolytic, 4.7 μfd. 63 V |
| C5,6 | Capacitor, Electrolytic, 1.0 μfd. 63 V |
| R1 | Resistor, Carbon Film, 47K ohm ¼ watt |
| R2,4 | Resistor, Carbon Film, 1.0K ohm ¼ watt |
| R3 | Resistor, Carbon Film, 200 ohm ¼ watt |
| R5 | Resistor, Carbon Film, 13K ohm ¼ watt |
| IC1 | Integrated Circuit, Waveform Generator |
| IC2 | Integrated Circuit, Voltage Regulator 12 V 1 amp |
| J1 | PC Connector, 44 pin |

It has been found that signals with frequencies from about 1 to 100 Hertz are effective. Preferably, signals with frequencies from about 3 to 50 Hertz are used. However, it is to be understood that it is possible to use higher or lower frequencies depending on the effectiveness to a particular local area of a particular body.

Figure 2:
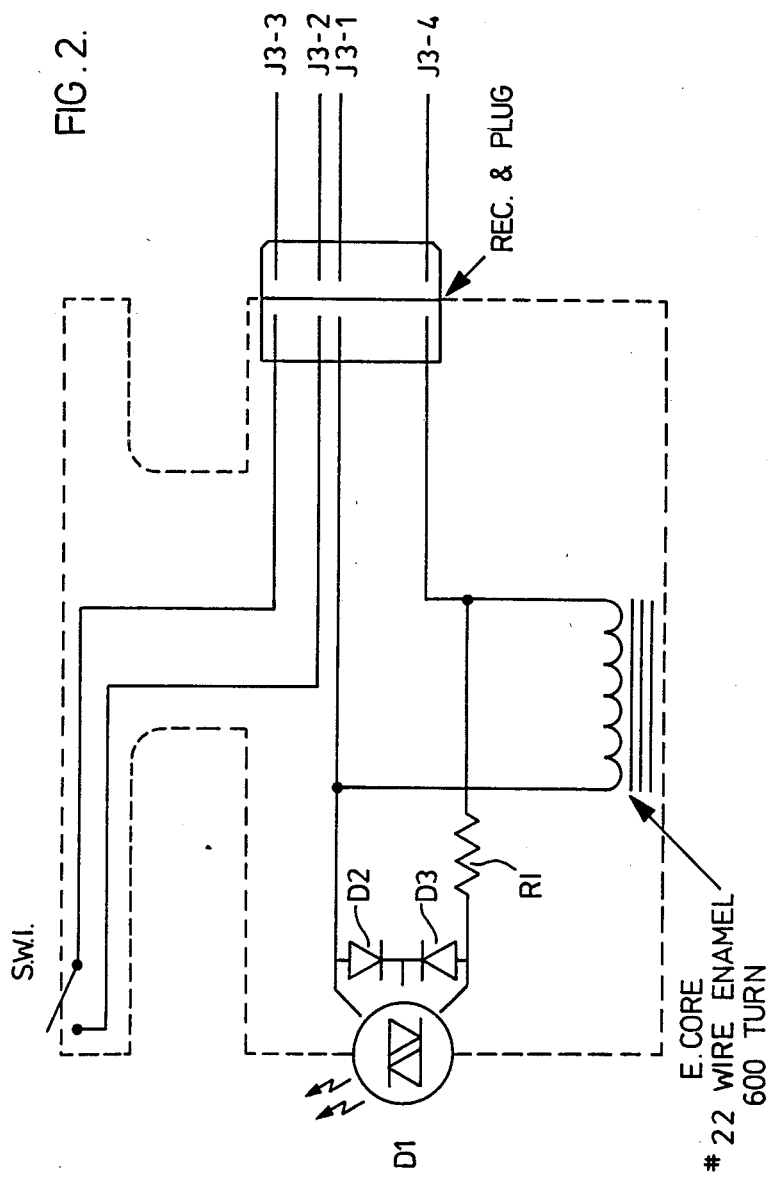
FIG. 2 is a schematic drawing of a treatment head for the present invention including an electric coil.

Shown in FIG. 2 is a schematic of a treatment head incorporating an electric coil. The treatment head is indicated by dashed lines. The coil in the treatment head can typically be made from #22 wire, enamelled, with about 600 turns. Also an "E" core can be used.

The core should be capable of developing a minimum of about 700 gauss at a location of about 1 centimeter away from the coil. It has been found that a coil capable of developing 1500 gauss at a comparable distance is effective. It is to be understood, however, that a higher level may also be effective.

Figure 3:
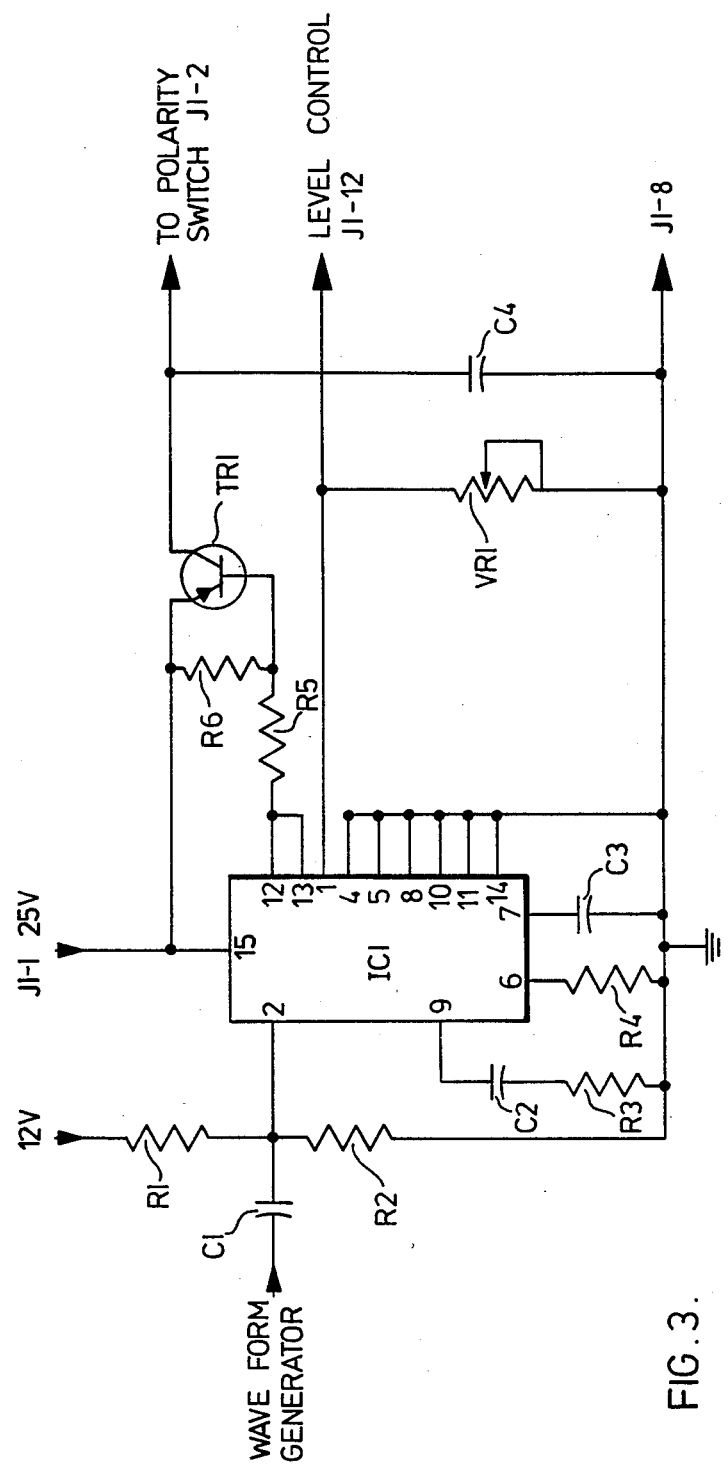
FIG. 3 is a schematic drawing of an output driver for use with this invention.

Shown in FIG. 3 is a typical output driver to be used with the present invention. Shown below in Table II are typical parts used in the construction of the circuit illustrated in FIG. 3.

TABLE II

| | |
|---|---|
| C1 | Capacitor, Electrolytic, 4.7 μfd. 63 V |
| C2 | Capacitor, Met. Film, .0033 μfd, 630 V |
| C3 | Capacitor, Electrolytic, 1.5 μfd. 63 V |
| C4 | Capacitor, Electrolytic, 100 μfd. 63 V |
| R1 | Resistor, Carbon Film, 2.0 M ohm ¼ watt |
| R2 | Resistor, Carbon Film, 110K ohm ¼ watt |
| R3 | Resistor, Carbon Film, 33K ohm ¼ watt |
| R4,6 | Resistor, Carbon Film, 10K ohm ¼ watt |
| R5 | Resistor, Carbon Film, 1.0K ohm ¼ watt |
| VR1 | Resistor, Variable, 4.7K ohm, .1 watt |
| TR1 | Transistor, Power Darlington |
| 1C1 | Integrated Circuit, Pulse Width Regulator |

In operation, the device of the present invention preferably should be used for about an average of 20 minutes per day with respect to a specific local area.

It has been found that there are two possible modes of operation with respect to the present invention if the current in the coil flows in only one direction. There is a negative mode and a positive mode. It has been found that immediately after an injury has occurred at a local area, treatment with the present invention in the negative mode is more effective than treatment in the positive mode. The negative mode is more effective while acute symptoms persist after an injury has occurred. On the other hand, if an injury displays chronic symptoms, it is more effective to use the device of the invention in the positive mode.

By negative mode is meant that if the north-seeking end of a compass needle is exposed to the magnetic field developed by the coil in the area of effective use, the north-seeking end of the compass needle will be attrached to the coil.

On the other hand, in the positive mode, the south-seeking end of the compass needle will be attracted to the coil.

The mode in which the device of the present invention is used is determined by the direction of the current flow through the coil.

It will be understood that the specific circuits and materials described herein are for illustration only and that the invention is not limited to those embodiments.

What I claim is:

1. An electromagnetic device for modifying any of the growth, repair or maintenance processes in a predetermined local area of a living body comprising:
    a coil capable of inducing a magnetic field wherein the magnetic field has a time-varying spatial-configuration and a time-constant spatial-orientation with respect to said coil;
    means for generating an electrical signal capable of exciting said coil so as to induce a magnetic field having a time-varying spatial-configuration, wherein said signal has a substantially-symmetric waveform with a frequency below about 100 Hertz; and
    wherein, when said device is in use, said coil is adapted such that the spatial-orientation of said magnetic field with respect to said local area is capable of being varied in time, thereby causing time variations in said magnetic field at any given location in said local area which are of about the same range of magnitude as time variations in the magnetic field at said any given location caused by the time variations in the spatial-configuration of said magnetic field.

2. A device as claimed in claim 1 wherein said signal is a pulsed signal.

3. A device as claimed in claim 1 wherein said signal is a half-wave-rectified sine wave.

4. A device as claimed in claim 1 wherein said signal has a waveform with a non-zero differential with respect to time.

5. A device as claimed in claim 1 wherein said signal has a waveform with symmetric discontinuities.

6. A device as claimed in claim 3 wherein said coil surrounds a magnetic core.

7. A device as claimed in claim 3 wherein said coil surrounds the middle finger of a core having an "E" shape.

8. A device as claimed in claim 7 comprising a treatment head wherein said treatment head comprises said coil and is capable of easy movement in a region over said local area.

9. A device as claimed in claim 8 wherein said treatment head is capable of easy manual manipulation.

10. A device as claimed in claim 9 wherein said treatment head is adapted to be gripped by a human hand in order to aid in easy manual manipulation.

11. A method of using a device as claimed in claim 9 comprising translating said coil in a region over said local area.

12. A method of using a device as claimed in claim 10 comprising translating said coil in a region over said local area.

13. A method of using a device as claimed in claim 9 comprising rotating said coil in the region of said local area.

14. A method of using a device as claimed in claim 10 comprising rotating said coil in the region of said local area.

15. A method of using a device as claimed in claim 9, wherein said device is in a negative mode.

16. A method of using a device as claimed in claim 10 wherein said device is in a negative mode.

17. A method of using a device as claimed in claim 9 wherein said device is in a positive mode.

18. A method of using a device as claimed in claim 10 wherein said device is in a positive mode.

* * * * *